(12) United States Patent
Magnusson

(10) Patent No.: US 7,481,805 B2
(45) Date of Patent: Jan. 27, 2009

(54) DRAINAGE CATHETER

(75) Inventor: Anders Magnusson, Uppsala (SE)

(73) Assignee: Innoventus Project AB (SE)

( * ) Notice: Subject to any disclaimer, the term of this patent is extended or adjusted under 35 U.S.C. 154(b) by 376 days.

(21) Appl. No.: 10/606,538

(22) Filed: Jun. 26, 2003

(65) Prior Publication Data

US 2004/0039339 A1 Feb. 26, 2004

Related U.S. Application Data

(60) Provisional application No. 60/391,667, filed on Jun. 27, 2002.

(51) Int. Cl.
*A61M 1/00* (2006.01)
*A61M 25/00* (2006.01)
*A61M 31/00* (2006.01)
*A61M 37/00* (2006.01)

(52) U.S. Cl. .................. 604/540; 604/95.04; 604/528; 604/541

(58) Field of Classification Search ......... 604/540–544, 604/528, 95.04, 530, 533
See application file for complete search history.

(56) References Cited

U.S. PATENT DOCUMENTS

| | | | |
|---|---|---|---|
| 4,740,195 A | 4/1988 | Lanciano | |
| 4,906,230 A * | 3/1990 | Maloney et al. | .......... 604/95.03 |
| 4,960,134 A | 10/1990 | Webster, Jr. | |
| 5,199,950 A | 4/1993 | Schmitt et al. | |
| 5,352,198 A | 10/1994 | Goldenberg et al. | |
| 5,399,165 A | 3/1995 | Paul, Jr. | |
| 5,928,208 A | 7/1999 | Chu et al. | |
| 6,033,378 A | 3/2000 | Lundquist et al. | |
| 6,217,528 B1 | 4/2001 | Koblish et al. | |
| 2001/0044625 A1 * | 11/2001 | Hata et al. | .................... 606/41 |
| 2001/0053890 A1 | 12/2001 | Osborne | |

FOREIGN PATENT DOCUMENTS

| | | | |
|---|---|---|---|
| WO | WO 93/04724 | * | 3/1993 |
| WO | WO 9304724 A1 * | | 3/1993 |
| WO | WO 99/10039 | | 3/1999 |

* cited by examiner

*Primary Examiner*—Tatyana Zalukaeva
*Assistant Examiner*—Melanie J Hand
(74) *Attorney, Agent, or Firm*—Fish & Richardson P.C.

(57) ABSTRACT

A catheter includes a tubular body, a ring member, and at least one elongate member. The tubular body has a distal region. The ring member encircles at least a portion of the circumference of the tubular member. The one elongate member has a proximal end and a distal end, the distal end of the elongate member being coupled to the distal region of the tubular body and the proximal end being attached to the ring member. Forming a loop in a distal end of a catheter includes pulling a ring that encircles at least a portion of the circumference of the catheter. The ring is attached to a proximal end of an elongate member, a distal end of the elongate member is attached to a distal end of the catheter, and the elongate member is positioned along the outside surface of the catheter.

20 Claims, 8 Drawing Sheets

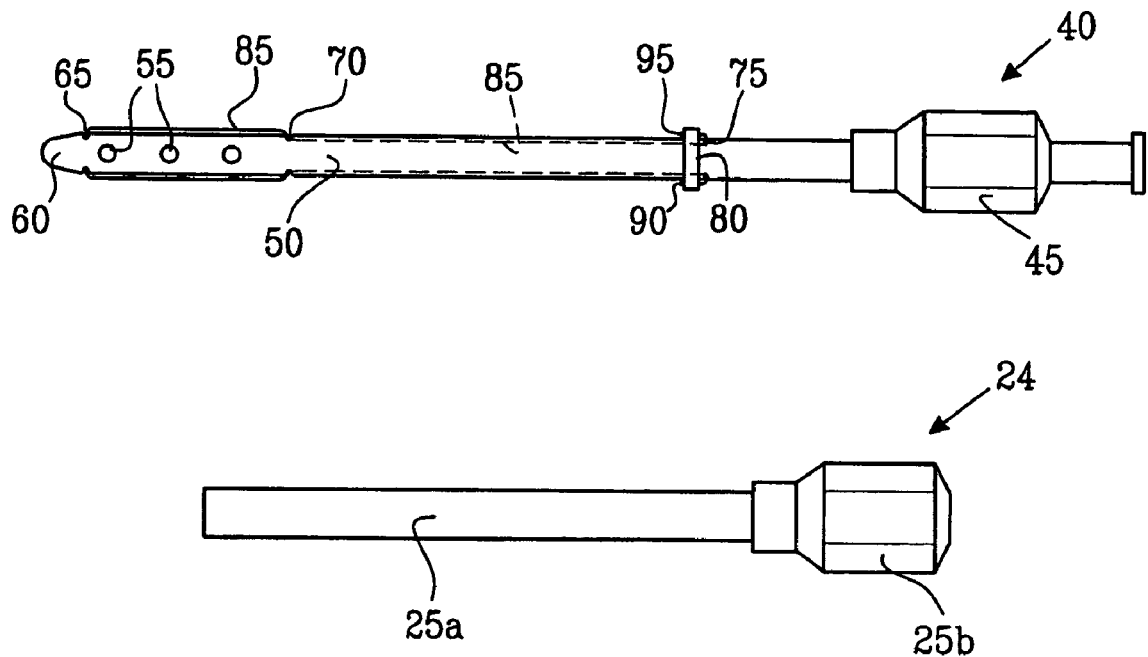
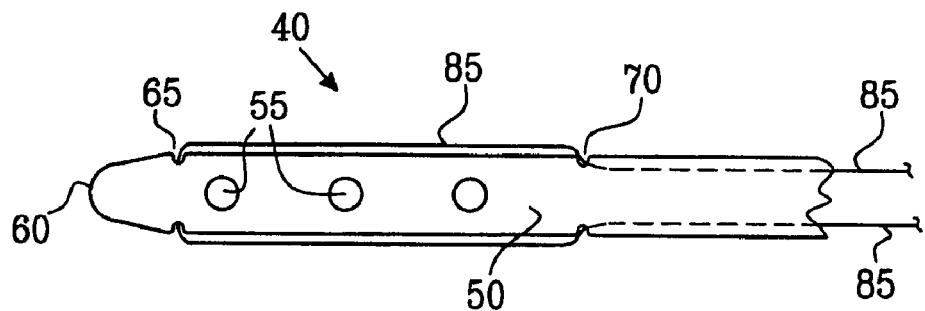
FIG.5a
FIG.5b
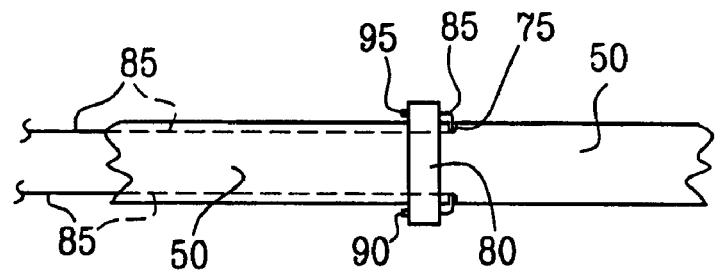
FIG.5c

DRAINAGE CATHETER

This application claims the benefit of priority under 35 U.S.C. §119(e) to U.S. provisional application 60/391,667, filed Jun. 27, 2002, which application is incorporated by reference in its entirety.

TECHNICAL FIELD

The present invention relates to medical devices for positioning in internal body cavities such as the collecting system in the kidney, the urinary bladder, etc. In particular, the invention relates to catheters for drainage purposes and means for securing such catheters in place.

BACKGROUND

In many medical conditions, it is necessary to drain or empty internal body cavities of liquids, e.g., urine, blood, etc. For this purpose, numerous designs of catheters are available and commonly used. If it is required that the drainage be performed over an extended period of time, such as several days, weeks or even months, it is essential that the catheter be properly secured inside the body cavity that is being drained. One common type of securable catheter is known as a Cope loop catheter or lockable "pig-tail" catheter. This catheter is characterized by including a means to form a curl (i.e., pig-tail) at its distal end once the catheter has been positioned inside the body cavity, thereby forming an efficient means to prevent or resist the catheter from being pulled out. For example, the curl can be formed by pulling a thread that is secured at the proximal end of the catheter and runs inside the catheter lumen to its distal tip, where it exits through an exit hole located in the vicinity of the catheter tip. The thread runs back along the outer surface of the catheter, enters the catheter again through a hole at a certain distance from the distal exit hole, and then passes inside the catheter to the proximal end of the catheter, where a "loose end" of the thread is available for a physician to grip and pull. Pulling the thread causes the two distally located holes to approach each other, thereby forming the curl.

Percutaneous nephrostomy is one of the oldest techniques used in interventional radiology. It comprises placing a drainage catheter or tube inside the renal pelvis through a skin insertion. The drainage catheter used for percutaneous nephrostomy typically is the "Cope loop" type drainage catheter described above. Early methods were very time consuming, requiring multiple procedural steps. In fact, the procedure could take up to a week to complete. However, the technique has been developed substantially and today the entire procedure is performed at one time in one continuous sequence of steps.

Despite the many advantages of the Cope loop catheter, in particular its very efficient locking function by virtue of the curl, it nevertheless still has certain disadvantages. For example, one problem with the Cope loop catheter is the potential difficulty in creating the desired loop, especially in an undilated system. In particular, the catheter tip sometimes gets stuck in a calyx or in the ureter and may require substantial manipulation before a locking curl is obtained.

Furthermore, because urine is a supersaturated solution of salts, the salt is easily crystallized from the solution when the solution comes into contact with a foreign material, such as the catheter material. If this happens, the catheter clogs and, because the pulling thread runs inside the lumen of the catheter, the thread may get stuck in the precipitated crystals. In this situation, it may be very difficult, if not impossible, to manipulate the locking thread to remove the curl and "unlock" the catheter. As a consequence, the physician may need to perform a more complicated and invasive intervention to remove the catheter.

SUMMARY

In a general aspect, the present application relates to a catheter comprising a tubular body, a ring member, and at least one elongate member. The tubular body has a distal region. The ring member encircles at least a portion of the circumference of the tubular member and is slidable along the tubular member. The one elongate member has a proximal end and a distal end, the distal end of the elongate member being coupled to the distal region of the tubular body and the proximal end being attached to the ring member.

Embodiments of the catheter may include one or more of the following features. For example, the tubular body may include an inner lumen, an outer surface, and a pair of openings passing between the outer surface and the inner lumen. The coupling of the elongate member to the distal region of the tubular body may include the elongate member passing through the pair of openings. The elongate member may pass between the ring member and the pair of openings along the outer surface of the tubular body.

The tubular body may include a second pair of openings passing between the outer surface and the inner lumen and positioned proximal to the first pair of openings. The elongate member passes between the first pair of openings and the second pair of openings along the outer surface and between the second pair of openings and the ring member along at least a portion of the inner lumen.

The tubular body may include a third pair of openings passing between the outer surface and the inner lumen and positioned proximal of the second pair of openings. The elongate member passes between the third pair of openings and the ring member along the outer surface.

The tubular body may include a loop positioned distal of the coupling of the elongate member to the distal region of the tubular body. The elongate member may also include a single length of a thread passing between the distal region of the catheter and the ring member.

The catheter can further comprise a connector piece being attached to a proximal region of the tubular body.

The distal region of the tubular body can define at least a first stiffness over a substantial portion thereof and a proximal region of the tubular body can define at least a second stiffness over a substantial portion thereof, which second stiffness is less than the first stiffness. The tubular body can further define at least the first stiffness from a distal end thereof to the proximal region defining the second stiffness.

In another general aspect, a catheterization kit is described including a catheter and an introducer. The catheter comprises a connector piece, a tubular body, at least one elongate member and a ring member. The tubular body has a distal region and a proximal region and the connector piece is attached to the proximal region of the tubular body. The elongate member has a proximal end and a distal end, the distal end of the elongate member being coupled to the distal region of the tubular body and the proximal end of the elongate member being attached to the ring member. The ring member is slidable along the tubular body. The introducer includes a connector piece and a sheath. The sheath has a longitudinal channel passing between a proximal end and a distal end, and the connector piece has a longitudinal channel and is joined to the proximal end of the sheath. The catheter connector piece is removably attachable to the introducer connector piece when the catheter is received within the introducer. The ring member abuts the proximal end of the introducer when the catheter is sufficiently positioned within the introducer, thereby causing the elongate member to become stretched.

Embodiments of the catheterization kit may include one or more of the following features. For example, the tubular body may include an inner lumen, an outer surface, and a pair of openings passing between the outer surface and the inner lumen. The coupling of the elongate member to the distal region of the tubular body includes the elongate member passing through the pair of openings. The elongate member may pass between the ring member and the pair of openings along the outer surface of the tubular body.

The tubular body may include a second pair of openings passing between the outer surface and the inner lumen and positioned proximal to the first pair of openings. The elongate member passes between the first pair of openings and the second pair of openings along the outer surface and between the second pair of openings and the ring member along at least a portion of the inner lumen.

The tubular body includes a third pair of openings passing between the outer surface and the inner lumen and positioned proximal of the second pair of openings, and the elongate member passes between the third pair of openings and the ring member along the outer surface.

The tubular body may include a loop positioned distal of the coupling of the elongate member to the distal region of the tubular body. The elongate member may be a single length of a thread passing between the distal region of the catheter and the ring member.

The distal region of the tubular body can define at least a first stiffness over a substantial portion thereof and the proximal region of the tubular body can define at least a second stiffness over a substantial portion thereof, which second stiffness is less than the first stiffness. The tubular body can further define at least the first stiffness from a distal end thereof to the proximal region defining the second stiffness.

The introducer may have a length that is approximately the same as a length of the elongate member between the attachment of the elongate member to the ring member and the coupling of the elongate member to the distal region of the tubular body, and the length may be between approximately 3 mm and 10 mm longer than the length of the introducer.

The ring member may be securable proximally of the introducer for stretching the elongate member. The elongate member may be securable by a fastening means provided on the proximal end of the introducer. The fastening means may be a clamping device. The clamping device may be a slot in which the elongate member is securable in a press fit.

The elongate member may extend from the point where it is coupled to the catheter and along the outer surface of the catheter. The fastening means may be a slit in which the elongate member is securable by frictional engagement. The elongate member may be coupled to the catheter at a finite distance from the distal tip of the catheter.

The catheterization kit may further include a needle having an inner lumen, a guide wire configured to fit within the inner lumen of the needle, a dilator having an inner lumen configured to pass over the guide wire and a guiding pin configured to fit within the tubular body. The dilator may include a radiopaque section positioned such that it is located at the distal end of the sheath of the introducer when the dilator is sufficiently positioned within the introducer.

In another general embodiment, a catheterization kit includes a catheter and an introducer. The catheter includes a tubular body, at least one elongate member and a stop. The tubular body has a distal region, the elongate member has a length, a proximal end and a distal end. The distal end of the elongate member is mounted to the distal region of the tubular body, and the proximal end of the elongate member is attached to the stop. The stop being slidable along the tubular body. The introducer includes a hub and a sheath. The sheath has a longitudinal channel passing between a proximal end and a distal end. The hub has a longitudinal channel and is joined to the proximal end of the sheath, and the joined hub and sheath have a length. The length of the elongate member is between approximately 3 mm and 10 mm longer than the length of the hub and sheath. The stop abuts the proximal end of the introducer when the catheter is sufficiently positioned within the introducer, thereby causing the elongate member to become stretched.

In another general aspect, forming a loop in a distal end of a catheter includes pulling a ring that encircles at least a portion of the circumference of the catheter. The ring is attached to a proximal end of an elongate member, a distal end of the elongate member is attached to a distal end of the catheter, and the elongate member is positioned along the outside surface of the catheter.

In another aspect, securing a catheter in a body cavity includes inserting an introducer into a body cavity, inserting a catheter into the introducer, advancing the catheter into the introducer, and attaching a catheter hub to an introducer hub. The introducer includes a hub and a sheath having a longitudinal channel passing between a proximal end and a distal end. The hub has a longitudinal channel and is joined to the proximal end of the sheath. The catheter includes a hub, a tubular body, at least one elongate member and a ring member. The tubular body has a distal region and a proximal region, and the hub is attached to the proximal region of the tubular body. The elongate member has a proximal end and a distal end, and the distal end of the elongate member is mounted to the tubular body in the distal region. The proximal end of the elongate member is attached to the ring member, and the elongate member passes along the outside surface of the catheter between the ring member and the distal region of the tubular body. The catheter is advanced into the introducer until the catheter hub is adjacent to the introducer hub. Advancing the catheter into the introducer causes the ring member to contact the introducer hub and form a loop in the distal region of the tubular body.

In another general aspect, forming a loop in a distal end of a catheter includes inserting an introducer into a body cavity, inserting a catheter into the introducer, advancing the catheter into the introducer until a ring member is adjacent to an introducer hub, and advancing the catheter into the introducer until the catheter hub is adjacent to the ring member.

The introducer includes a hub and a sheath having a longitudinal channel passing between a proximal end and a distal end. The hub has a longitudinal channel and is joined to the proximal end of the sheath. The joined hub and sheath have a length. The catheter includes a hub, a tubular body, at least one elongate member and a ring member. The tubular body has a distal region, the elongate member has a length, a proximal end and a distal end. The distal end of the elongate member is mounted to the distal region of the tubular body and the proximal end of the elongate member is attached to the ring member. Advancing the catheter into the introducer until the catheter hub is adjacent to the ring member causes the ring member to contact the introducer hub and form a loop in the distal region of the tubular body.

The length of the elongate member is between approximately 3 mm and 10 mm longer than the length of the hub and sheath.

In another general aspect, changing drainage catheters in a body cavity includes inserting an introducer into a body cavity, inserting a first drainage catheter into the introducer, advancing the first drainage catheter into the introducer, removably connecting a catheter hub to an introducer hub and using the first drainage catheter to drain fluids from the body cavity. The drawing may further include disconnecting the catheter hub from the introducer hub, withdrawing the first drainage catheter from the introducer while leaving the introducer within the body cavity, and inserting a second drainage catheter into the introducer.

The introducer includes the introducer hub and a sheath having a longitudinal channel passing between a proximal end and a distal end. The hub has a longitudinal channel and is joined to the proximal end of the sheath. The first drainage catheter includes the catheter hub, a tubular body, at least one elongate member and a ring member. The tubular body has a distal region and a proximal region. The catheter hub is attached to the proximal region of the tubular body. The elongate member has a proximal end and a distal end. The distal end of the elongate member is mounted to the tubular body in the distal region, the proximal end of the elongate member is attached to the ring member, and the elongate member passes along the outside surface of the first drainage catheter between the ring member and the distal region of the tubular body. The first drainage catheter is advanced into the introducer until the catheter hub is adjacent to the introducer hub and a loop is formed in the body cavity by the distal region of the first drainage catheter.

In another general aspect, drawing an internal body cavity includes inserting an introducer into a body cavity, inserting a first drainage catheter into the introducer, advancing the first drainage catheter into the introducer, removably connecting a catheter hub to an introducer hub and using the first drainage catheter to drain fluids from the body cavity. The drawing may further include disconnecting the catheter hub from the introducer hub, withdrawing the first drainage catheter from the introducer while leaving the introducer within the body cavity, and inserting a second drainage catheter into the introducer.

The introducer includes the introducer hub and a sheath having a longitudinal channel passing between a proximal end and a distal end. The hub has a longitudinal channel and is joined to the proximal end of the sheath. The first drainage catheter includes the catheter hub, a tubular body, at least one elongate member and a ring member. The tubular body has a distal region and a proximal region. The catheter hub is attached to the proximal region of the tubular body. The elongate member has a proximal end and a distal end. The distal end of the elongate member is mounted to the tubular body in the distal region, the proximal end of the elongate member is attached to the ring member, and the elongate member passes along the outside surface of the first drainage catheter between the ring member and the distal region of the tubular body. The first drainage catheter is advanced into the introducer until the catheter hub is adjacent to the introducer hub and a loop is formed in the body cavity by the distal region of the first drainage catheter.

In another general aspect, drawing a first and a second internal body cavity includes inserting an introducer into a body cavity, inserting a first drainage catheter into the introducer, advancing the first drainage catheter into the introducer, removably connecting a catheter hub to an introducer hub, using the first drainage catheter to drain fluids from the body cavity, disconnecting the catheter hub from the introducer hub, withdrawing the first drainage catheter from the introducer while leaving the introducer within the body cavity, and inserting a second drainage catheter into the introducer.

The introducer includes the introducer hub and a sheath having a longitudinal channel passing between a proximal end and a distal end. The hub has a longitudinal channel and is joined to the proximal end of the sheath. The first drainage catheter includes the catheter hub, a tubular body, at least one elongate member, a ring member and a first loop positioned distal of the coupling of the elongate member to the distal region of the tubular body. The tubular body has a distal region and a proximal region. The catheter hub is attached to the proximal region of the tubular body. The elongate member has a proximal end and a distal end. The distal end of the elongate member is mounted to the tubular body in the distal region, the proximal end of the elongate member is attached to the ring member, and the elongate member passes along the outside surface of the first drainage catheter between the ring member and the distal region of the tubular body. The first drainage catheter is advanced into the introducer until the catheter hub is adjacent to the introducer hub and the first loop is positioned within the first body cavity and a second a loop is formed in the second body cavity by a part of the distal region of the first drainage catheter.

The catheter can provide numerous advantages. For example, the catheter can be used to easily and simply form a loop in a body cavity—even in those cavities in which the available space is restricted or limited. Another advantage of the catheter is that exchange of catheters is very easily performed. In particular, the exchange typically will not necessitate the use of auxiliary equipment, such as guide wires, anesthesia, and fluoroscopy. Furthermore, the exchange of catheters can be performed by a nurse outside a hospital, and a doctor need not supervise the procedure.

A further advantage is that if the pulling thread is arranged to extend along the outside of the catheter tubing, the risk of clogging by precipitation of salt from, e.g., urine, causing the thread to get stuck, is eliminated. This will reduce or eliminate the problem associated with prior art Cope-loop catheters in which the thread extends inside the catheter.

The details of one or more embodiments of the invention are set forth in the accompanying drawings and the description below. Other features and advantages of the invention will be apparent from the description, the drawings, and the claims.

DESCRIPTION OF THE DRAWINGS

FIG. 5a is a side view of a second embodiment of a drainage catheter and introducer for draining a body cavity.

FIG. 5b is an enlarged side view of the distal tip of the catheter of FIG. 5a.

FIG. 5c is an enlarged side view of the middle section of the catheter of FIG. 5a illustrating a slidable ring and attached pulling threads.

Like reference symbols in the various drawings indicate like elements.

DETAILED DESCRIPTION

Figure 1A:
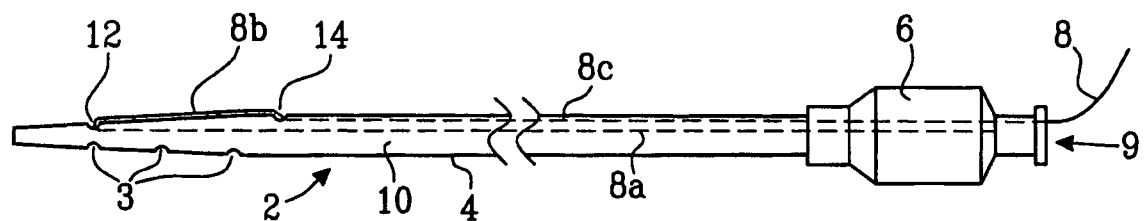
FIG. 1a is a side view of a prior art Cope-loop catheter.
Figure 1B:
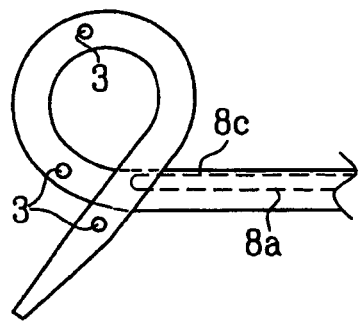
FIG. 1b is an enlarged side view of the distal tip of the catheter of FIG. 1a illustrating a loop formed in the distal tip of the catheter.

FIGS. 1a and 1b illustrate a prior art Cope loop locking catheter 2. The catheter 2 includes a tube 4 in which the drainage liquid flows. The distal end of the tube 4 includes a plurality of drainage openings 3 for entry into the catheter of the liquid to be removed. The tube 4 is made of a suitable, flexible polymer material, such as polyurethane. The proximal end of the tube 4 is attached to a connector piece, such as a hub 6. A pulling thread 8 runs from a proximal end opening 9 of the tube 4 to which it is fixed through the inside of a catheter lumen 10. A first portion 8a of the thread extends to the distal end region of the tube 4 where it penetrates the tube wall at a first point of penetration 12. A second portion 8b of the thread extends back along the exterior of the tube 4 to a second point of penetration 14, where it again enters the lumen 10 of tube 4. From the second point of penetration, a third portion 8c of the thread extends back to and through the hub 6, where it exits at the very proximal end of the tube 4.

The term "distal" is herein defined as far from an introduction point of the catheter into the body, while the term "proximal" is herein defined as nearer an introduction point of the catheter into the body. For example, the distal end of the catheter indicates the end of the catheter intended to be positioned within the body, while the proximal end of the catheter indicates the end of the catheter intended to be positioned at or near the introduction point or outside the body. The term "distal region" is herein used to indicate a region being intended to be positioned inside the body far from an introduction point of the catheter, while the term "proximal region" is herein used to indicate a region positioned nearer the introduction point. Furthermore, the proximal and distal end of an elongate member or a thread are herein used to indicate the part/parts of the thread being adapted to be positioned proximally and distally respectively, i e the distal end of the thread can be a real end or part of the thread, for example the middle region of the thread, being adapted to be positioned distally.

If the physician pulls the part of the thread 8 extending from the connector 6, the first point of penetration 12 will be pulled in the direction of the second point of penetration 14. If the physician continues to pull the thread 8, the distal end of the catheter 2 will form a loop (i.e., "pig-tail") (FIG. 1b). In this position the section 8b of the thread will have decreased its length to virtually zero. The loop, if correctly formed inside the cavity in which the catheter has been inserted, will provide a reliable means to prevent the catheter from being pulled out.

The procedure for positioning the Cope loop locking catheter 2 involves penetration of the kidney, dilatation of the incision, and thereafter inserting the catheter 2 in the dilated tissue channel. Thus, the catheter rests in the dilated channel in direct contact with the kidney tissue.

As indicated above, a drawback with this prior art catheter 2 is that it can be difficult to create the loop because the catheter 2 must be inserted into the cavity to be drained to a sufficient extent that will allow a full loop to be created. In so doing, the catheter 2 can get stuck in various irregularities in the cavity, such as a calyx or the ureter when the cavity is the renal pelvis. If the catheter 2 is stuck in an irregularity, there is insufficient space to create the loop because, for example, the distal end will not be able to loop back on itself when the thread 8 is pulled by the physician.

Figure 2A:
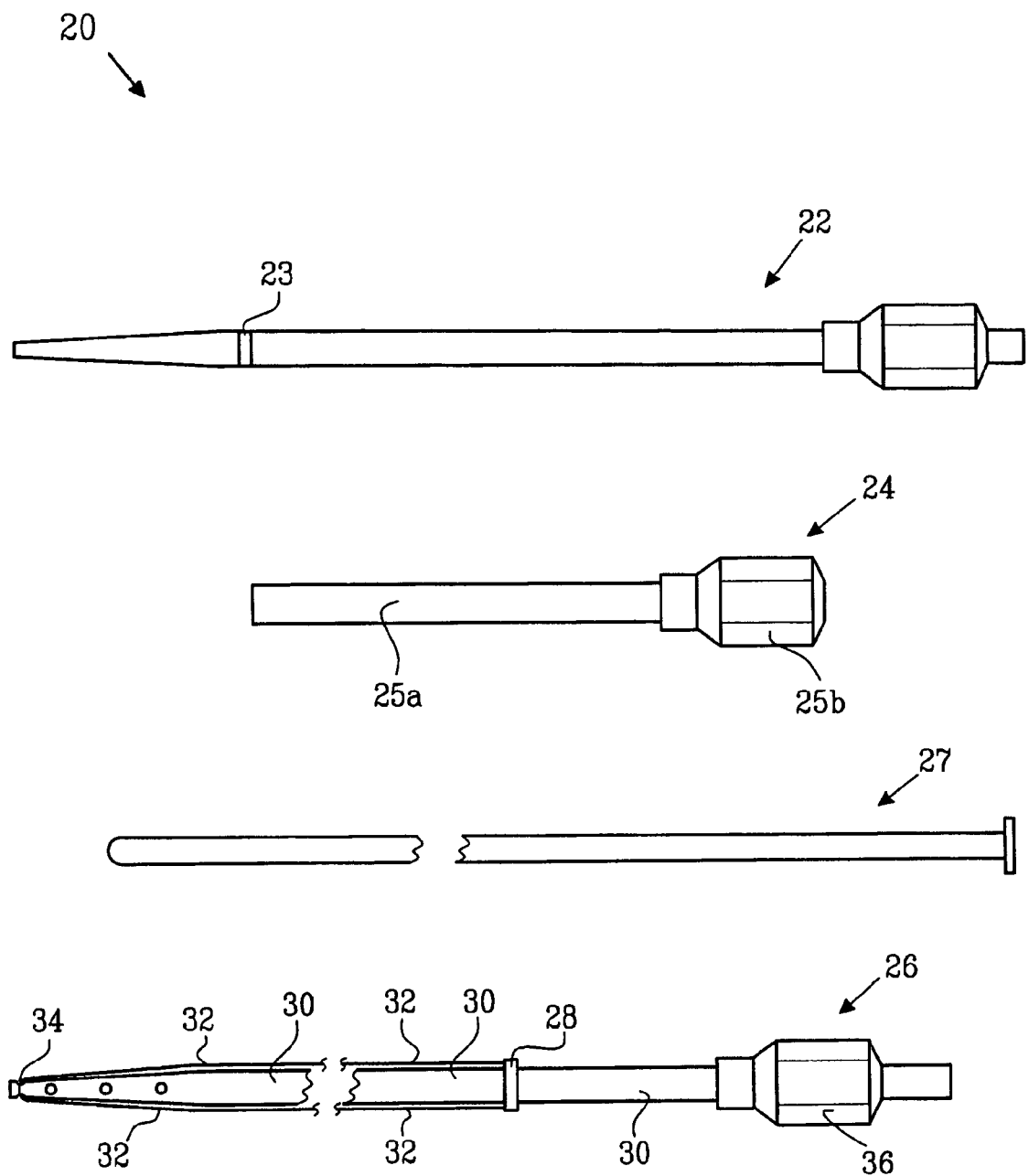
FIG. 2a is a side view of a set of medical devices that includes a dilator, an introducer, a mandril, and a catheter used for draining a body cavity.

Referring to FIG. 2a, a set of medical devices 20 includes a dilator 22, an introducer 24, a pig-tail (or Cope-loop type) catheter 26, and a guiding pin or mandril 27. The introducer 24 includes a sleeve 25a and a connector piece, such as hub 25b. As described below in more detail, the dilator 22 is used to position the device within a cavity to be drained. The catheter 26 has a pulling means 28 (e.g., ring member, stop, or stopping device) that is configured to interact with the hub 25b of the introducer 24. The stopping device 28 may be in the form of a ring or ring member that is slidingly attached on the catheter tubing 30. From the ring 28, an elongate member or pulling thread 32 runs to a distal point of attachment 34 at the distal end of the catheter 26 (or to a point near the distal end), where it penetrates the catheter tubing 30, exits on, for example, the opposite side, and runs back and attaches to the ring 28. The pulling thread 32 penetrates the catheter tubing 30 by simply pulling the thread through the tubing at the tip, e.g., by means of a needle to puncture the tubing, or by making a hole in the catheter and then pulling the thread therethrough. The pulling thread is generally non-elastic so that the loop can be reliably formed. Although the pulling thread 32 is coupled to the catheter tubing 30 by passing it through a pair of openings in the tubing, it may be coupled to the catheter by any other suitable means, such as a metal band, an adhesive or a knot.

The dilator 22 includes a radiopaque section 23. For example, this section can be made of a metal having the desired radiopacity, e.g., platinum (Pt) or gold (Au), although any method and/or material of providing radiopacity is acceptable to provide this function. The position of the radiopaque section 23 on the dilator 22 is selected such that when the dilator 22 is positioned within the introducer 24 the radiopaque section 23 is located just at the distal end of the sleeve 25a. As described in more detail below, the radiopaque section 23 permits a physician to ensure under fluoroscopy that the introducer 24 is positioned within the collecting system.

Although fluoroscopy is one method of visualizing the introducer within the body cavity, ultrasound techniques also can be used to visualize the placement of the medical devices (i.e., introducer, needle, guide wire, dilator, catheter) within the body cavity. Ultrasound techniques for visualizing these devices within body cavities are well-known to those of skill in the art.

The catheter 26, the introducer 24, and the dilator 22 are fabricated from commonly used medical grade plastics using standard techniques. For example, the plastic can be one or more of polyurethane, polypropylene, polyethylene, nylon, polyethylene terephthalate, polyethen, Hd-polyethen, latex, and any other suitable polymer, as well as a Pebax® material. Furthermore, the catheter 26 can be fabricated of more than one material. Materials having different stiffness can be used to produce a catheter 26 having different stiffness in different regions. Preferably, a distal region of the catheter 26 comprising the portion of the catheter 26 adapted to form a loop defines a stiffness which is greater than the stiffness of a proximal region of the catheter 26 comprising the portion of the catheter 26 adapted to be positioned within the introducer 24 when a loop is formed. The materials having different stiffness can be welded together or unified through melting. Alternatively, a process can be used wherein the stiffness of the material can be regulated during injection moulding of the catheter 26. If desired, the catheter 26 can be produced having different thickness in different sections. A memory metal or a spring metal can also be used in the catheter 26.

The guiding pin or mandril 27 can be made from any medical grade metal or polymer. The metal can be, for example, stainless steel, nitinol, or titanium. The polymer can be one or more of the polymers described above. The pulling thread 32 can be made from for example nylon.

Figure 2B:
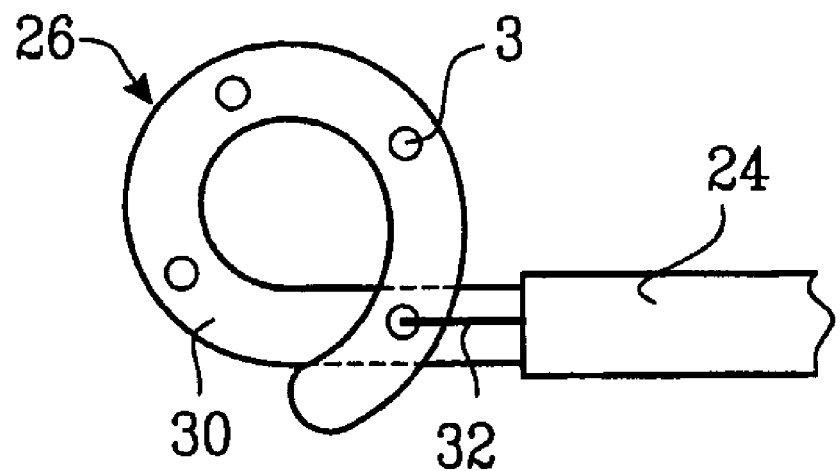
FIG. 2b is an enlarged side view of the distal tip of the catheter of FIG. 2a illustrating a loop formed in the distal tip of the catheter when the thread extends to the distal tip of the catheter.
Figure 2C:
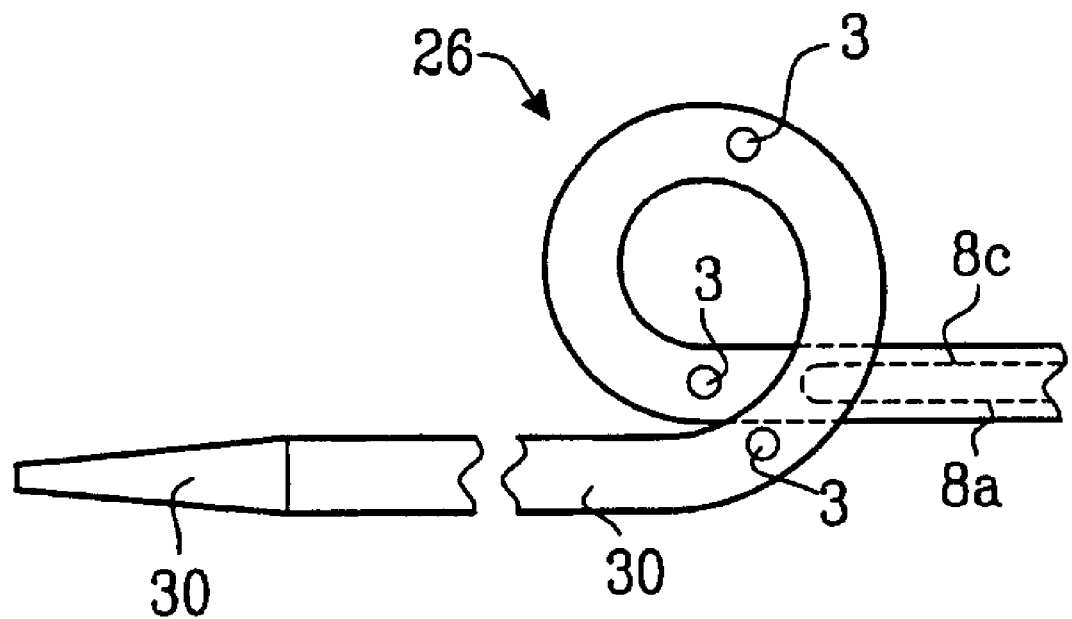
FIG. 2c is an enlarged side view of the distal tip of the catheter of FIG. 2a illustrating a loop formed in the distal tip of the catheter when the thread extends to a middle region of the catheter.

Referring to FIGS. 2b and 2c, the catheter 26 can be configured to form a loop anywhere along the length of the tubing 30 based upon the position at which the thread 32 passes through the tubing. For example, FIG. 2b illustrates the thread 32 passing through the tubing 30 at a position that is at the distal end of the catheter 26. FIG. 2c illustrates the thread 32 passing through the tubing 30 at a position that is proximal of the distal end of the catheter 26 by a set distance. As such, when the loop is formed, the tubing 30 extends beyond the loop by the set distance at which the thread passes through the catheter 26.

Figure 3:
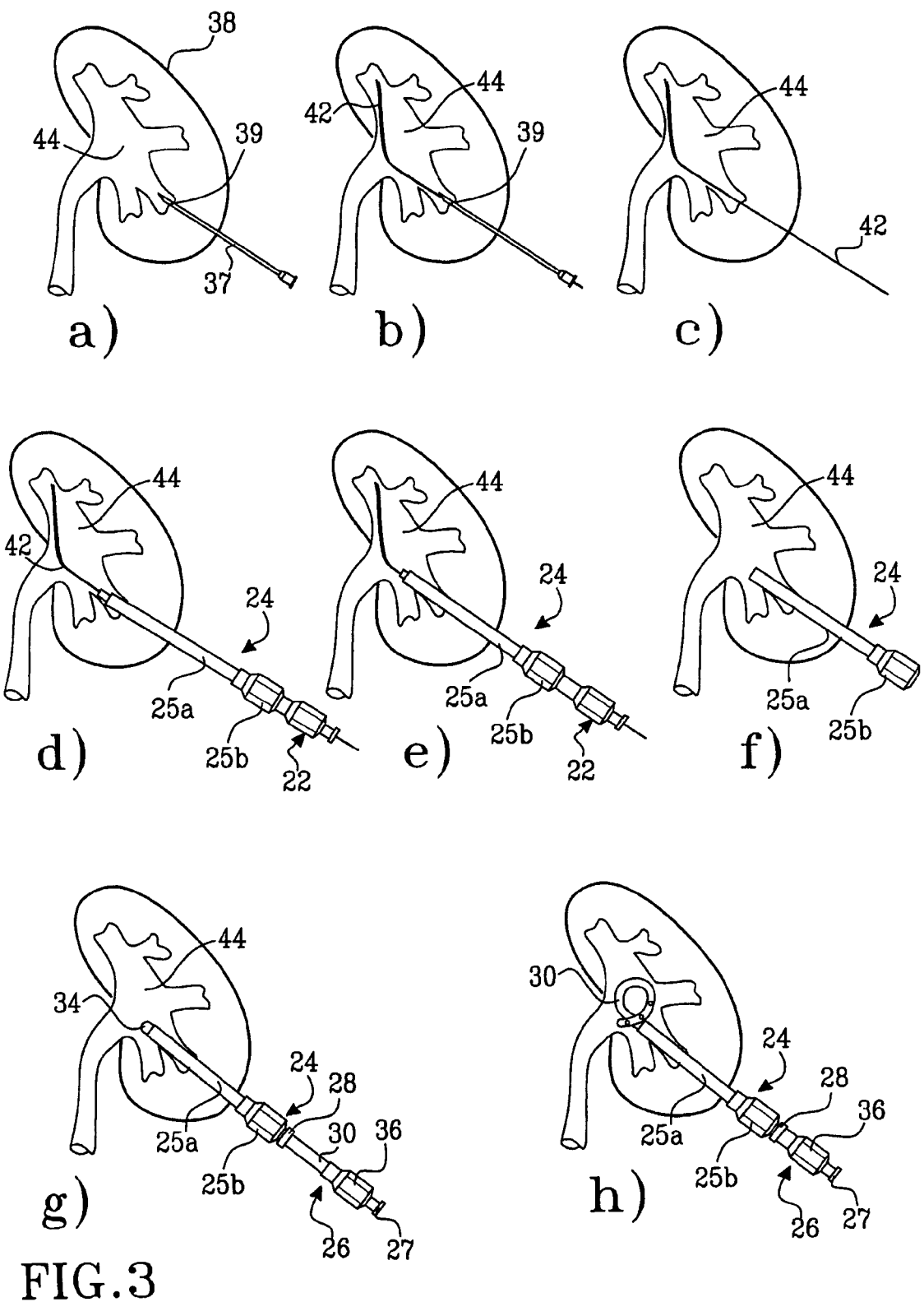
FIGS. 3a-h illustrate the procedure for using the set of medical devices of FIG. 2a for placing the catheter of FIG. 2a in the renal pelvis.

The set of medical devices 20 are used to place the catheter 26 in a body cavity to drain the body cavity. For example, referring to FIGS. 3a-h, the catheter 26 can be positioned in the renal pelvis for the purpose of draining the renal pelvis. Initially, a hollow needle 37 is used to percutaneously puncture the kidney 38 to provide an access path to the collecting system 39, such as the renal pelvis. The penetration is done such that the needle enters into a calyx 39 (FIG. 3a). A guide wire 42 is then passed through the lumen of the hollow needle 37 such that it extends into the collecting system, which corresponds to a distance of about 4 cm to 5 cm beyond the tip of the needle 37 (FIG. 3b). With the guide wire 42 in position within the body cavity, the needle then is withdrawn (FIG. 3c). The dilator 22 next is inserted into the introducer 24, and the assembly of the dilator and the introducer is passed over the guide wire 42 and inserted into the kidney tissue (FIG. 3d). Passing the assembly into the tissue widens or dilates the channel created initially by the needle 37. To dilate the tissue in as atraumatic a manner as possible, there should be a smooth transition between the introducer sleeve 25a and the extension of the dilator 22 out from the introducer sleeve. For example, the distal tip of the introducer sleeve 25a can be tapered to have an inner diameter that is minimally larger than the outer diameter of the dilator 22. This is most easily achieved by tapering the distal end of the sleeve 25a to a fairly small angle, such as less than approximately 45°, preferably less than 30°, most preferably less than 20°. In general, the smaller the angle the better, and only manufacturing techniques limit the angle value. Of course, if the sleeve 25a is made from a material that is thin enough, a taper may not be needed at all if there is a very close fit of the dilator 22 within the sleeve 25a. To decrease the friction between the introducer 24 and the dilator 22 a hydrofil friction coating may be applied on the dilator 22. The dilator 22 may be connected to the hub 25b of the introducer 24 through a hub at the proximal end of the dilator 22. Furthermore, the distal end of the dilator 22 is preferably formed as a sharp edge and the inner diameter of the dilator 22 matches the diameter of the guide wire.

The assembly of the dilator 22 and the introducer 24 then are advanced slightly forward into the collecting system at which point the physician optionally verifies under fluoroscopy, ultrasound, or x-ray that the radiopaque section 23 is positioned within the collecting system (FIG. 3e). Because the dilator 22 is located inside the introducer 24 such that the radiopaque section 23 is located just at the distal end of the sleeve 25a, the physician can ascertain when the sleeve 25a has been positioned just inside the collecting system by looking for the radiopaque section under fluoroscopy. The dilator 22 then is withdrawn, which leaves the introducer in position within the collecting system (FIG. 3f).

The catheter 26 is next introduced into the introducer 24 (FIG. 3g). To ease the introduction of the catheter into the introducer, the rigid guiding pin 27 is first inserted into the catheter to provide longitudinal rigidity and support to the catheter. In this manner, the catheter 26 has less of a tendency to get stuck in the introducer 24, which otherwise might occur due to the flexibility of the catheter.

To decrease the friction between the introducer 24 and the catheter 26 a friction reducing coating may be applied on the catheter tubing 30. Furthermore, an O-ring is preferably placed between the hubs 36 and 25b to make the connection leak proof.

Generally, the introducer 24 as well as the assembled introducer-catheter subsystem has to be smooth and bend easily without collapsing.

When the catheter 26 has been inserted into the introducer 24 to a point where the ring 28 abuts the hub 25b of the introducer 24, as shown in FIG. 3g, the thread 32 will become tight or slightly stretched. The thread 32 is stretched because the length of the introducer is approximately the same as the length of the thread from the point of abutment of the ring 28 against the hub 25b and to the point of attachment of the thread at the catheter distal end 34 where it just exits the sleeve 25a. Because the thread 32 is stretched and cannot be elongated due to its lack of elasticity, and because the distal point of attachment 34 cannot move further away from the distal tip of the introducer, advancing the catheter further into the introducer creates a loop in the tubing 30. During the formation of the loop, the guiding pin 27 should be removed to prevent it from interfering with the loop. Alternatively, the guiding pin 27 can be kept in place but it should not be advanced together with the catheter 26.

As a consequence of advancing the catheter 26 further into the introducer 24, the catheter tubing 30 behind the point 34 will therefore begin to be expelled out from the introducer and extend past the point 34, whereby the loop will start to form (FIG. 3h). The physician advances the catheter 26 until the hub 36 of the catheter mates with the corresponding hub 25b of the introducer. At this position the hubs 36 and 25b, respectively, can be coupled together, e.g., by a thread engagement, a bayonet type lock or by any other suitable locking means. In this manner, the catheter is locked into position within the collecting system (i.e., renal pelvis) with the loop effectively anchoring the catheter within the kidney.

The procedure of placing the catheter 26 can be summarized as follows: (1) use a needle to create a channel through tissue to the cavity to be drained; (2) insert a guide wire through the needle and advance the guide wire into the cavity; (3) remove the needle and pass a dilator and an introducer over the guide wire and dilate the tissue; (4) remove the dilator and pass a catheter having a pulling thread attached at its distal end over the guide wire and into the catheter; (5) stop the insertion of the catheter when the point of thread attachment is located just beyond the distal catheter opening; (6) ascertain that the thread is stretched and that it is secured in a stretched position; (7) advance the catheter further into the introducer to begin to form a loop at the distal catheter opening; (8) couple the catheter and introducer to each other after a loop of a desired size has been formed; and, optionally, (9) secure the introducer/catheter assembly to the patient's skin.

In general, steps (5) and (6) are automatically performed by virtue of the pulling thread 32 being attached to the ring 28, which functions as a stopping means when it abuts the hub 25b of the introducer. The desired size of the loop also is automatically obtained by adapting the length of the catheter such that the desired loop size is formed when the catheter hub 36 just abuts the introducer hub 25b, or when the two hubs have been properly coupled to each other, e.g., by threading or by a bayonet type lock or the like.

More broadly the procedure of placing the catheter 26 can be performed by: (1) dilating the tissue surrounding the body cavity to form a channel therein; (2) positioning an introducer tube in the channel; (3) inserting a catheter having a pulling thread attached at its distal end into the introducer; (4) ascertaining that the pulling thread is stretched and that it is secured in a stretched position when the point of thread attachment is located just beyond the catheter exit opening; (5) advancing the catheter further into the introducer to thereby form a loop at the distal catheter opening; and (6) locking the catheter in the position when a loop of a desired size has been formed.

Figure 4A:
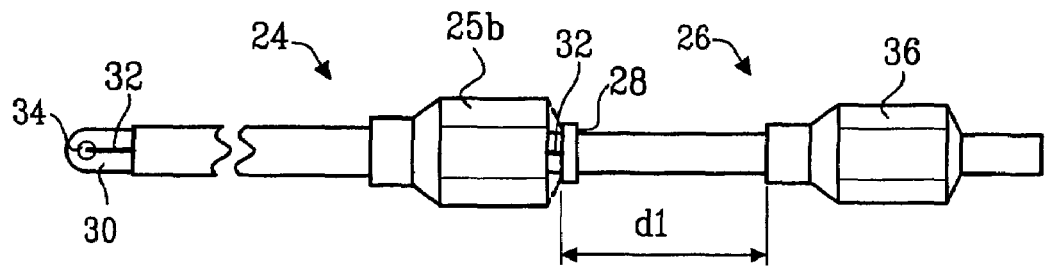
FIGS. 4a-d illustrate the formation of the loop that results from the interaction between the ring and the hub of the introducer.

FIGS. 4a-d illustrate the interaction between the catheter 26 and the introducer 24 that is a key to forming the loop. Initially, the catheter 26 is advanced within the introducer 24 until the ring 28 rests against the connector 25b (FIG. 4a). At this point, the distal tip of the catheter extends slightly out of the introducer and the pulling thread is tight. The distance between the connector 25b and the connector 36 is $d_1$, which is specified to be approximately the circumference of the loop to be formed. Moreover, as the catheter is advanced the combination of the catheter extending beyond the introducer and the distance between the two connector pieces 25b, 36 will be approximately d1.

Figure 4B:
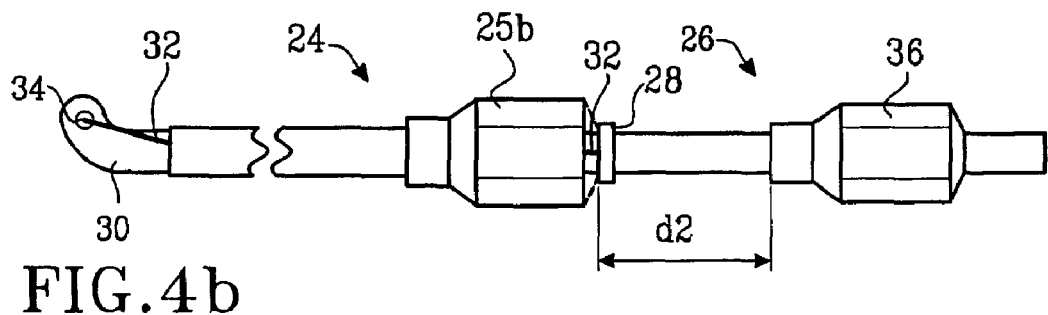
Figure 4C:
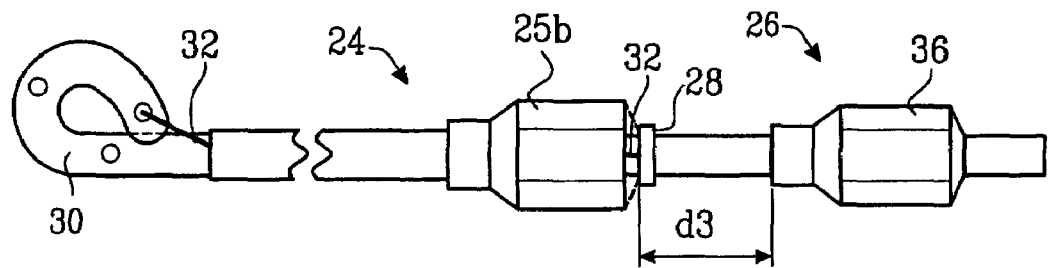

The physician then advances the catheter 26 slightly further into the introducer 24. Because the ring 28 is resting against the connector 25b and because the pulling thread 32 is already tight, further advancing the catheter 26 causes the start of the loop to be formed (FIG. 4b). As the catheter is advanced, the distance $d_1$ is reduced to a distance $d_2$. As described above, the reduction in distance $d_1$ is approximately the same as the amount by which the catheter extends beyond the introducer. As the catheter 26 is further advanced within the introducer 24, the pulling thread 32 remains a generally constant length, which keeps the distal end of the catheter adjacent to the distal tip of the introducer. Thus, the catheter tubing 30 begins to form a larger loop as it is advanced though the introducer (FIG. 4c). As the distance $d_2$ is reduced to a distance $d_3$, an approximately equal amount is advanced through the introducer.

Figure 4D:
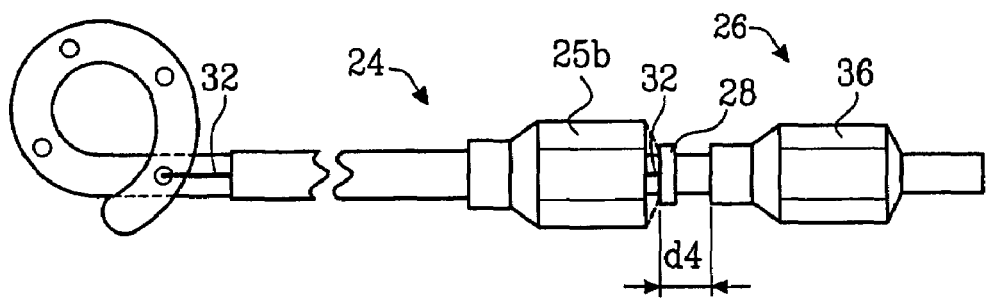

Finally, completely advancing the catheter 26 into the introducer 24 traps the ring 28 between the connector pieces 25b, 36 and reduces the distance $d_3$ to $d_4$ (FIG. 4d). The circumference of the loop when the ring 28 is trapped between the connector pieces 25b, 36 is approximately $d_1$. The circumference of the loop can be set by increasing or decreasing the length of the pulling thread 32. For example, to increase the circumference of the loop, the length of the pulling thread should be reduced and to decrease the circumference of the loop, the length of the pulling thread should be increased.

In general, the introducer 24 has a length that is approximately the same as a length of the elongate member or pulling thread 32 that passes between the attachment of the elongate member to the pulling means or ring and the coupling of the elongate member to the distal region of the tubular body. More particularly, the length of the elongate member or pulling thread 32 that passes between the attachment of the elongate member to the pulling means or ring and the coupling of the elongate member to the distal region of the tubular body is between approximately 3 mm and 10 mm longer than the length of the introducer.

An advantage of the medical devices 20 described herein is that the catheter 26 can be easily changed if, for example, the catheter becomes clogged. In fact, the catheter 26 can be changed by a nurse without any auxiliary means and equipment, such as anesthesia. In particular, the catheter 26 is changed out as follows. Initially, the nurse or physician simply releases the lock between the introducer 24 and the catheter 26 and withdraws the catheter from the introducer. Withdrawing the catheter 26 causes the loop to automatically begin to reduce its size. Withdrawing the catheter 26 until it does not extend beyond the introducer completely eliminates the loop. Because the pulling thread 32 runs along the outside of the catheter 26 in the space between the introducer's inner wall and the catheter's outer surface, it is unlikely that any salts will precipitate enough to fix the thread to the catheter or introducer. Precipitation of salts causing fixation of the thread to the catheter is the most common problem with prior art catheters because the thread runs almost entirely inside the catheter.

When the catheter 26 has been removed, a new catheter 26 is provided, the guiding pin 27 is inserted into the catheter lumen to render the catheter stiff enough for adequate pushability, and the catheter then is reinserted. The guiding pin 27 then is removed or retracted, and the catheter 26 is advanced into the introducer 24 such that the loop begins to form at the distal tip of the catheter.

Although the medical devices 20 will function very well as described above, modifications can be made that also will function very well. For example, the thread 32 does not necessarily need to be secured to the ring 28. Instead, the thread 32 can be provided as a single thread, attached at the distal end of the catheter tubing 30, but not secured at its proximal end. Instead of securing the proximal end to the ring, the thread should be securable to, for example, the connector pieces 25b and/or 36. In such an implementation, there should be some indicator mark on the thread that identifies when the distal point of attachment of the thread is located as desired, namely, just beyond the distal exit opening of the catheter tube. This identification can be achieved by a simple color mark positioned on the thread, or on the tube, such that the marking will reach the proximal insertion opening in the introducer hub or connector piece 25b exactly when the distal point of attachment of the thread to the tubing 30 has reached its desired position. At this point, the physician or nurse secures the loose thread end on the introducer hub 25b by any suitable means, such as, for example, a clamp provided on the connector or inserting the thread into a very narrow slit in the connector into which the thread can be forced to fit in a frictional engagement by virtue of its diameter being larger than the width of the slit. Many other securing means will work as long as they provide secure fixation of the thread to the hub 25b.

Referring to FIGS. 5a-c, in a further implementation, a drainage catheter 40 that is configured to be used with the introducer 24 includes a connector 45 and tubing 50. The tubing 50 includes openings 55 at a distal end 60 of the catheter 40 for draining fluid. The tubing 50 also includes a first set of openings 65 at the distal end 60 of the catheter, a second set of openings 70 that are proximal to the first set of openings 65, and a third set of openings 75 that are proximal to the second set of openings 70. The drainage catheter 40 also includes a stop member or ring 80 that is slidably mounted to the tubing 50.

The drainage catheter 40 differs from the drainage catheter 26 in part because a pulling thread 85 passes from outside of the catheter to the inside of the catheter and then back to the outside of the catheter. Specifically, the pulling thread 85 has two ends 90, 95, both of which are attached to the ring 80, for example, using a knot, adhesive, or other attaching means. The pulling thread 85 passes from the ring 80 into the third set of openings 75 and passes inside the inner lumen of the catheter 40. The pulling thread 85 passes out of the lumen of the catheter through the second set of openings 70. The pulling thread 85 then runs along the outside of the catheter 40 until it reaches the first set of openings 65, at which point the thread passes through the first set of openings into the lumen of the catheter. The distance between the first set of openings 65 and the second set of openings 70 is approximately the circumference of the loop that is formed when the catheter 40 is inserted into the introducer 24. The distance between the third set of openings 75 and the connector 45 is approximately the same as the distance between the first set of openings 65 and the second set of openings 70. By passing the pulling thread 85 into the second set of openings 70, the pulling thread will not rub against the distal end of the introducer when the catheter 40 and introducer 24 are positioned within the body cavity. This is advantageous because it extends the life of the thread and limits that mode of failure as a reason for replacing the catheter.

Figure 5D:
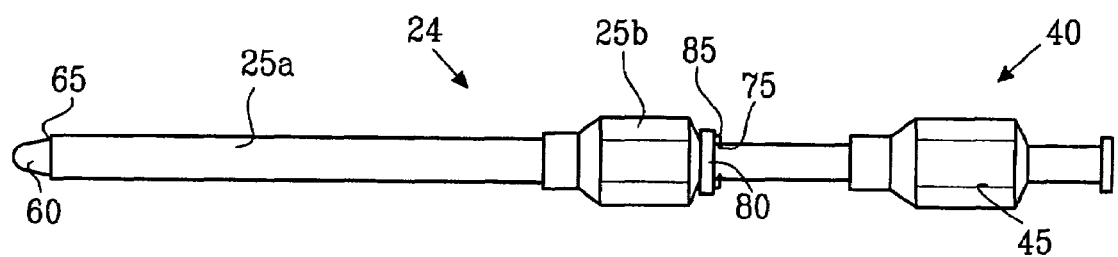
FIG. 5d is a side view of the drainage catheter of FIG. 5a inserted into the introducer.

Referring to FIG. 5d, in use, the catheter 40 is advanced into the introducer 24, which is already positioned within a body cavity, until the connector 25b contacts the ring 80, at which point the pulling thread 85 becomes taut. Further advancing the catheter 40 into the introducer 24 causes the connector 25b to push the ring 80 along the catheter tube 50 in the direction of the connector 45.

Figure 5E:
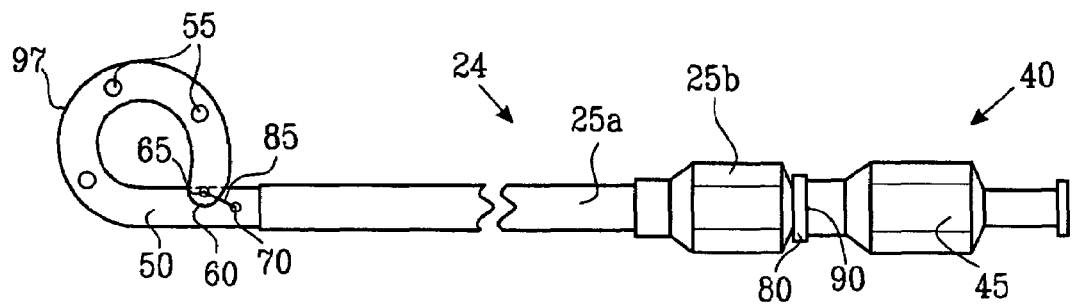
FIG. 5e is a side view of the drainage catheter of FIG. 5a further inserted into the introducer such that a loop is formed.

Referring to FIG. 5e, completely advancing the catheter 40 into the introducer 24 until the connector 25b, ring 80, and connector 45 are compressed together causes a loop 97 to form at the distal end 60 of the catheter 40. The second set of openings 70 are positioned along the length of the catheter tube 50 at a distance from the distal end such that the distal end of the introducer is proximal to the openings 70 when the catheter 40 is completely advanced into the introducer 24. In this manner, the pulling thread 85 is not likely to be rubbed by the distal end of the introducer 24 over the extended period in which the catheter 40 and introducer 24 are left within the body cavity. Continuous or regular rubbing of the distal end of the introducer 24 against the pulling thread 85 may damage the pulling thread and cause it to break.

Although FIG. 5a illustrates a particular distance between the second pair of openings 70 and the third pair of openings 75, the distance can be increased or decreased. For example, the distance can be set at approximately one centimeter by placing the third pair of openings closer to the distal end 60 such that the pulling thread is within the inner lumen of the catheter 40 for only that one centimeter. This advantageously reduces the length of pulling thread that can have salts deposited upon it, which, as described above, can cause the pulling thread to be fixed in place against the inner lumen of the catheter. Even if only one centimeter of pulling thread is fixed against the inner lumen, it is likely that the physician will be able to easily loosen that fixation and remove the loop in the catheter so that the physician can easily withdraw the catheter from the introducer.

Figure 6A:
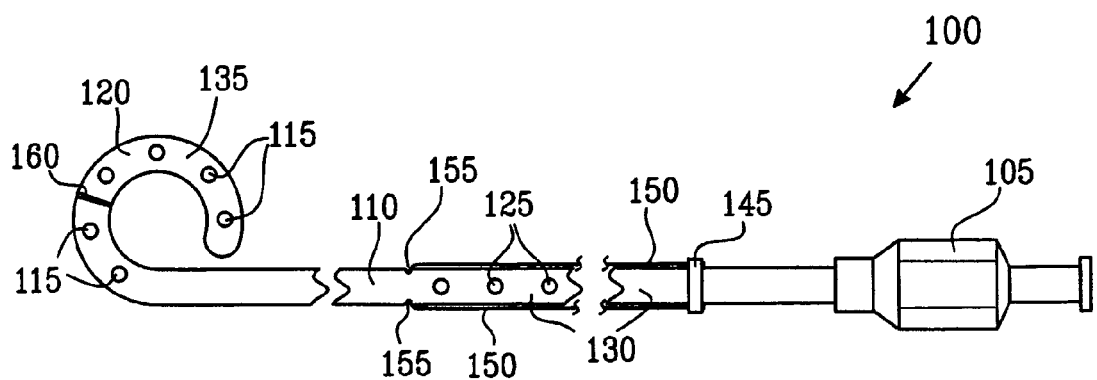
FIG. 6a is a side view of a drainage catheter for draining two body cavities, wherein a loop is formed at the distal end and the thread extends to a middle section of the catheter.
Figure 6B:
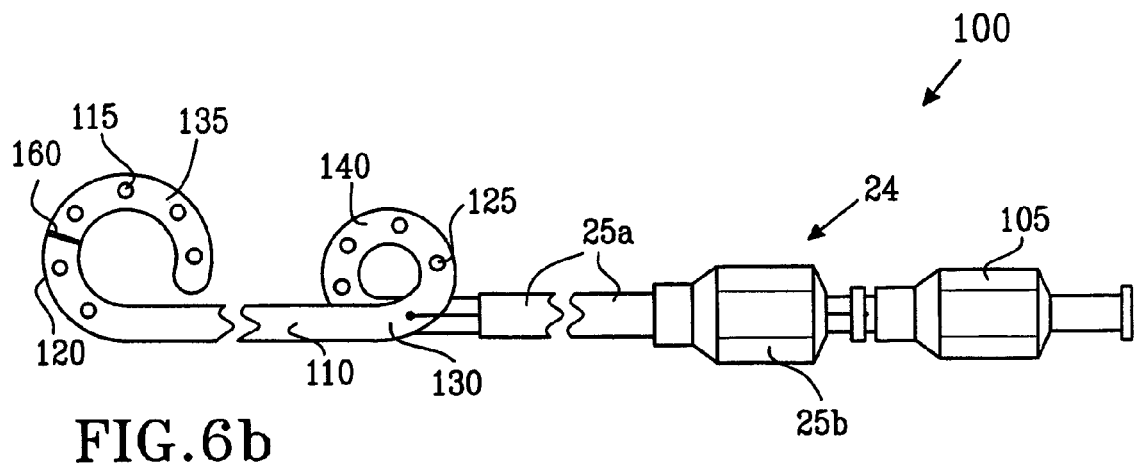
FIG. 6b is a side view of the drainage catheter of FIG. 6a inserted into an introducer such that a loop is formed in a middle section of the catheter.

Referring to FIGS. 6a and 6b, in a further implementation, a drainage catheter 100 that can drain two body cavities is configured to be used with the introducer 24 and includes a connector 105 and tubing 110. The tubing 110 includes a first set of openings 115 at a distal end 120 for draining fluid in a first body cavity and a second set of openings 125 at a middle section 130 for draining fluid in a second body cavity. The first set of openings 115 are formed within a first loop 135 and the second set of openings 125 are formed within a second loop 140. The first loop 135 is formed in the tubing 110 using standard methods, e.g., placing the catheter 100 over a curved mandril and placing the assembly in a heat oven to impart the curve in the mandril to the catheter. The catheter 100 also includes a ring 145, a pulling thread 150, and openings 155 through which the pulling thread passes. Advancing the catheter 100 into the introducer 24 causes the ring 145 to slidingly move along the tubing 110 and form the loop 140. The catheter 100 also may include a radiopaque band 160 mounted to the first loop 135 such that the placement of the catheter 100 can be viewed under fluoroscopy to ensure that the first loop is correctly positioned within the first body cavity to be drained.

The catheter 100 is used, for example, to drain the kidney and the bladder. The catheter 100 is inserted in a manner similar to the drainage catheters described above. Initially, however, the first loop 135 is straightened to pass through the introducer 24. Optionally, the catheter 100 can be placed over a guide wire. In either case, the catheter 100 is advanced until the first loop 135 is within the bladder. In so doing, the introducer connector 25b pushes the ring 145 and forms the second loop 140 within the kidney.

In a further implementation, it is not necessary that the pulling thread be fixed or secured near the distal tip of the catheter. If it is desirable to drain the kidney (collecting system) at a point further down in the kidney, e.g., closer to the ureter, it is necessary to provide a relatively long tip that reaches as much as up to approximately 10 cm beyond the point of entry into the collecting system. Nonetheless, it is advantageous to position the loop at that entry point into the collecting system to provide a reliable fixation. The point of fixation of the thread on the catheter is located just beyond the distal opening of the introducer tube.

Figure 7:
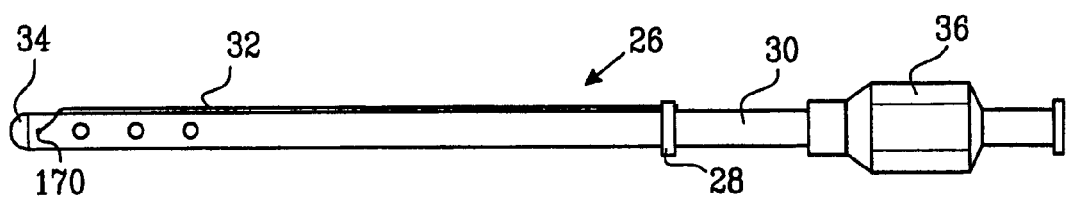
FIG. 7 is a side view of a drainage catheter have a single pulling thread.

A number of embodiments of the locking loop catheter have been described. Nevertheless, it will be understood that various modifications may be made without departing from the spirit and scope of the invention. For example, referring to FIG. 7, the thread 32 that extends along both sides of the tubing 30 can be configured to extend along only one side of the tubing by attaching one end of the thread to the distal tip end 34 and the other end to the stopping device or ring 28. This would, however, require an attachment means 170 at the tip, e.g., by a knot, by gluing, metal band, or molding, etc., to ensure that the end of the thread is securely attached to the tubing. The metal band can be a radiopaque metal band such that it is visible under fluoroscopy. The pulling thread, although shown running along the outside of the catheter, can be configured to run both inside and outside the catheter in the manner described above with respect to the drainage catheter 40 of FIG. 5a. Similarly, although the catheters have been described with reference to application in catheterization of the renal pelvis, it is to be understood that the catheter have broader application than use only in the renal pelvis. For example, the catheters will function equally well for draining other body cavities of a human or an animal, such as but not limited to the urinary bladder, the gall bladder, abscesses, peritoneal and thoracic cavity. Accordingly, other embodiments are within the scope of the following claims.

What is claimed is:

1. A catheter, comprising:
   a tubular body having a distal region;
   a stop member encircling at least a portion of the circumference of the tubular body, the stop member being slidable along the tubular body;
   at least one elongate member having a proximal end and a distal end, the distal end of the elongate member being coupled to the distal region of the tubular body and the proximal end being directly attached to the stop member; and
   wherein the tubular catheter body, stop member and elongate member are configured such that inserting the tubular catheter body into an introducer causes interaction between the stop member and the introducer to pull the elongate member to form a loop in the distal region of the tubular catheter body.

2. The catheter of claim 1, wherein the tubular body includes an inner lumen, an outer surface, and a pair of openings extending between the outer surface and the inner lumen and the coupling of the elongate member to the distal region of the tubular body comprises the elongate member passing through the pair of openings.

3. The catheter of claim 2, wherein the elongate member extends between the stop member and the pair of openings along the outer surface of the tubular body.

4. The catheter of claim 1, wherein the elongate member comprises a single length of a thread extending between the distal region of the catheter and the stop member.

5. The catheter of claim 1, further comprising a connector piece being directly attached to a proximal region of the tubular body.

6. The catheter of claim 1, wherein the distal region of the tubular body defines at least a first stiffness over a substantial portion thereof and a proximal region of the tubular body defines at least a second stiffness over a substantial portion thereof, which second stiffness is less than the first stiffness.

7. The catheter of claim 6, wherein the tubular body defines at least the first stiffness from a distal end thereof to the proximal region defining the second stiffness.

8. A catheter comprising:
   a first elongate member having a distal region;
   a protruding member slidably coupled to the first elongate member and extending outward from an outer surface of the first elongate member;
   a second elongate member having a proximal end and a distal end, the distal end of the second elongate member being coupled to the distal region of the first elongate member and the proximal end of the second elongate member being directly attached to the protruding member; and
   wherein the protruding member and first and second elongate members are configured such that sliding of the first elongate member relative to the protruding member upon insertion of the catheter into an introducer pulls the second elongate member to form a loop in the distal region of the first elongate member.

9. The catheter of claim 8, wherein the first elongate member includes an inner lumen, an outer surface, and a pair of openings extending between the outer surface and the inner lumen and the coupling of the second elongate member to the distal region of the first elongate member comprises the second elongate member passing through the pair of openings.

10. The catheter of claim 9, wherein the second elongate member extends between the protruding member and the pair of openings along the outer surface of the first elongate member.

11. The catheter of claim 8, wherein the second elongate member comprises a single length of a thread extending between the distal region of the catheter and the protruding member.

12. The catheter of claim 8, further comprising a connector piece being directly attached to a proximal region of the first elongate member.

13. The catheter of claim 8, wherein the distal region of the first elongate member defines at least a first stiffness over a substantial portion thereof and a proximal region of the first elongate member defines at least a second stiffness over a substantial portion thereof which second stiffness is less than the first stiffness.

14. The catheter of claim 13, wherein the first elongate member defines at least the first stiffness from a distal end thereof to the proximal region defining the second stiffness.

15. The catheter of claim 1, wherein inserting the tubular catheter body into an introducer causes interaction between the stop member and the introducer to pull the elongate member to form the loop in the distal region of the tubular catheter body.

16. The catheter of claim 1, wherein the length of the elongate member may be adjusted to adjust the degree of advancement required to pull the elongate member to form a loop in the distal region of the tubular catheter body.

17. The catheter of claim 1, wherein the loop formed in the distal region of the tubular catheter body includes more than 180 degrees of curvature.

18. The catheter of claim 8, wherein the protruding member is configured to interacts with the introducer upon insertion of the catheter to cause the first elongate member to slide relative to the protruding member to form the loop; and wherein the protruding member is further conflaured such that continued interaction with the introducer maintains the formed loop.

19. The catheterof claim 8, wherein the length of the second elongate member is adjustable to adjust the range of sliding of the protruding member along the first elongated member to pull the distal portion of the first elongate member into the loop.

20. The. catheter of claim 8, wherein the loop formed in the distal region of the first elongate member includes more than 180 degrees of curvature.

* * * * *

UNITED STATES PATENT AND TRADEMARK OFFICE
CERTIFICATE OF CORRECTION

PATENT NO.         : 7,481,805 B2                                           Page 1 of 1
APPLICATION NO. : 10/606538
DATED              : January 27, 2009
INVENTOR(S)        : Anders Magnusson It is certified that error appears in the above-identified patent and that said Letters Patent is hereby corrected as shown below:

In Claim 8, (column 15, line 57) delete "arc" and replace with "are"

In Claim 18, (column 16, line 43) delete "interacts" and replace with "interact"

In Claim 18, (column 16, line 46) delete "conflaured" and replace with "configured"

In Claim 19, (column 16, line 49) delete "catheterof" and replace with "catheter of"

In Claim 20, (column 16, line 54) delete "The." and replace with "The"

Signed and Sealed this

Twenty-fourth Day of March, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,481,805 B2
APPLICATION NO. : 10/606538
DATED : January 27, 2009
INVENTOR(S) : Magnusson Page 1 of 1

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by (376) days Delete the phrase "by 376 days" and insert -- by 283 days --

Signed and Sealed this

Eleventh Day of August, 2009

David J. Kappos
*Director of the United States Patent and Trademark Office*